Figure 1:
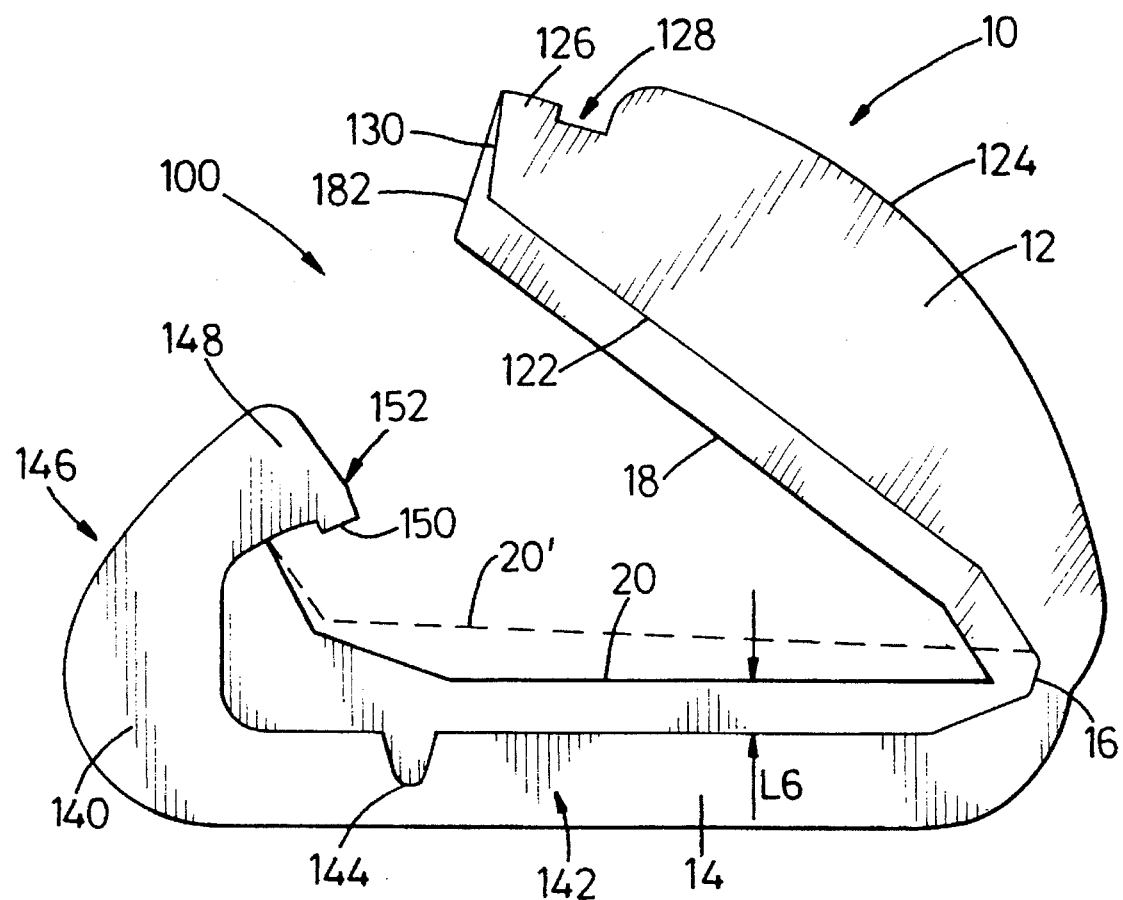

United States Patent [19]

McQuilkin et al.

[11] Patent Number: 5,575,802
[45] Date of Patent: Nov. 19, 1996

[54] MEDICAL CLIP

[75] Inventors: Peter H. McQuilkin; Marcus Filshie, both of Nottingham, England

[73] Assignee: Femcare (Cyprus) Limited, Limassol, Cyprus

[21] Appl. No.: 369,402

[22] Filed: Jan. 5, 1995

[30] Foreign Application Priority Data

Jan. 15, 1994 [GB] United Kingdom .................. 9400739

[51] Int. Cl.⁶ .............................................. A61B 17/04
[52] U.S. Cl. ........................ 606/151; 606/120; 606/157; 128/831; 128/843
[58] Field of Search .............................. 606/120, 151, 606/157, 158; 128/843, 831

[56] References Cited

U.S. PATENT DOCUMENTS

| 4,418,694 | 12/1983 | Beroff et al. | 606/158 |
| 4,424,810 | 1/1984 | Jewusiak | 606/158 |
| 4,822,348 | 4/1989 | Casey | 606/157 |
| 4,942,886 | 7/1990 | Timmons | 606/157 |
| 4,988,355 | 1/1991 | LeVeen et al. | 606/158 |
| 5,282,812 | 1/1994 | Suarez, Jr. | 606/158 |

FOREIGN PATENT DOCUMENTS

| 0087941 | 9/1983 | European Pat. Off. . |
| 0087940 | 9/1983 | European Pat. Off. . |

*Primary Examiner*—Gary Jackson
*Attorney, Agent, or Firm*—Salter & Michaelson

[57] ABSTRACT

The clip which is suitable for sexual sterilization or other medical use is constructed from a single plastic moulding with a silicone rubber lining. The clip has a front latch which comprises a pivotable section of the lower jaw which ensures positive latching of the clip.

10 Claims, 2 Drawing Sheets

MEDICAL CLIP

The present invention relates to medical clips and more particularly to clips suitable for sexual sterilisation devices which may be used as a sexual sterilisation clip adapted to be clamped on a Fallopian tube or vas deferens to effect occlusion. Hereinafter the clip will be referred to as a sterilisation clip but it is to be understood that the clip may be used for other purposes.

It is an object of the present invention to provide sterilisation clips (as defined) which may be manufactured with a frame constructed from plastics material.

It is a further object of the present invention to provide sterilisation clips which may be manufactured with a frame comprising a single piece of plastics material.

It is an additional object to provide a sterilisation clip having a positive front latching means.

The present invention provides a medical clip for use as a sexual sterilisation clip having a lower jaw member and an upper jaw member hingedly connected at one end to the lower jaw member, and comprising an internal silicone rubber lining, the upper and lower jaw members being provided at an opposite end thereof in relation to the hinge, with co-operating latch means comprising interlocking members in the upper and lower jaws to secure the clip in a closed position, the lower jaw being provided with a second hinge proximate to the co-operating latch means which enables the latch end of the lower jaw to pivot at the position of the second hinge.

Preferably the lower jaw comprises an elongate relatively straight portion comprising the main portion of the lower jaw conjoined with a U-shaped portion forming the latch means on the lower jaw, the main portion and the U-shaped portion being formed by the second hinge.

Preferably the latch means is arranged to lock the clip in a closed position, the clip being re-openable by squeezing the upper and lower jaws together and by pushing the latch formed by the lower jaw off the lower jaw.

Preferably both the upper and lower jaws are lined internally with silicone rubber.

Figure 2:
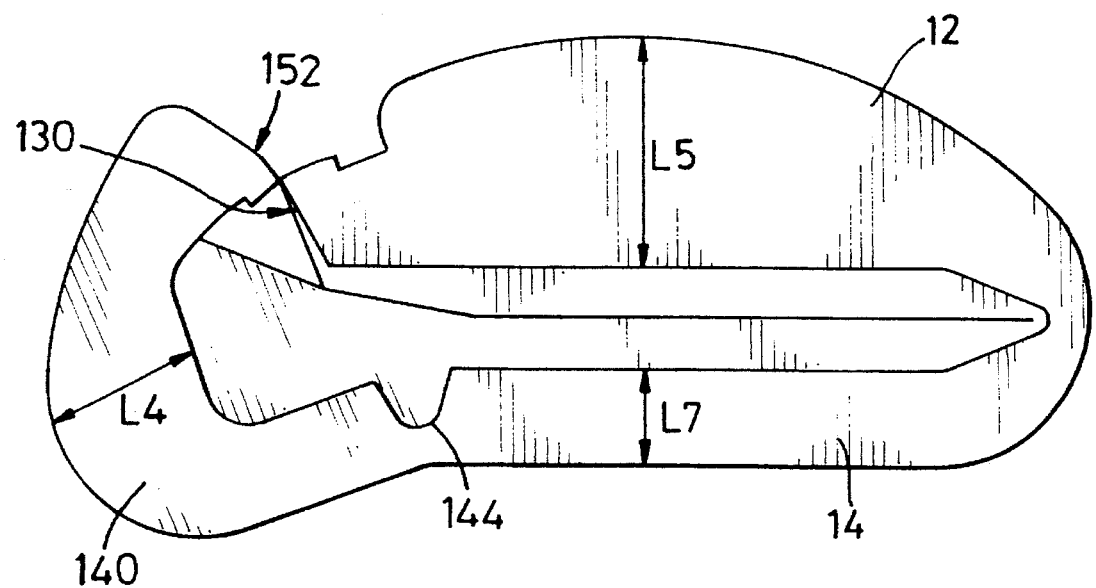
Figure 3:
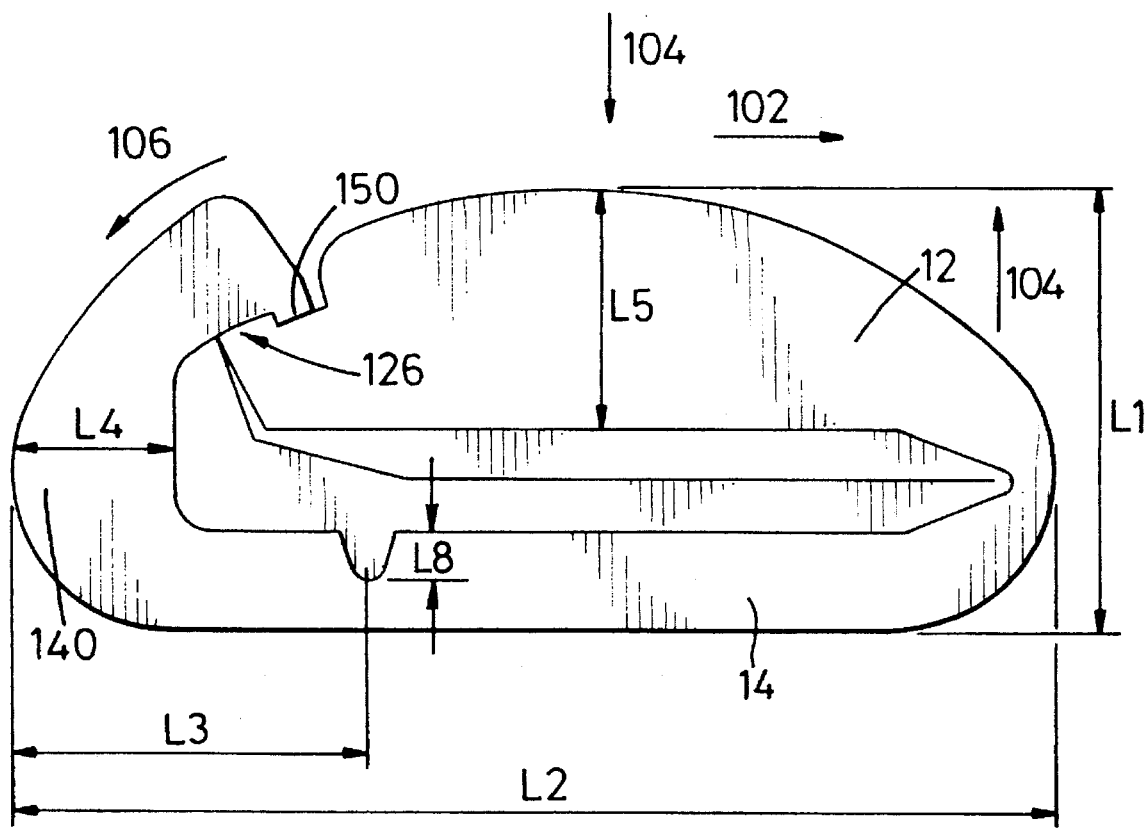

Embodiments of the present invention will now be described by way of example with reference to the accompanying drawings in which:

FIG. 1 shows in side elevation a clip according to the present invention in an open condition, FIG. 2 shows the clip of FIG. 1 in a partially closed condition, and FIG. 3 shows the clip of FIG. 1 in a fully closed condition.

With reference now to FIG. 1, the clip 10 comprises an upper jaw 12 and a complex lower jaw 14 which are joined together at a first hinge end 16. The first hinge comprises a thinner section of the plastics material from which the upper and lower jaws are constructed, thereby allowing a unitary construction.

The upper jaw 12 is thus pivotable about the first hinge 16 relative to the lower jaw 14.

The jaws 12, 14 are lined with a silicone rubber lining 18, 20. The lining is in a preferred embodiment made in one piece. The lower portion 20 of the lining is shaped to conform to the inside of a U-shaped portion 140 of the lower jaw member 14. The complex bottom jaw 14 therefore comprises two portions, an elongate relatively straight portion 142 and a U-shaped latch portion 140.

The two portions 140, 142 are joined by a second hinge 144 which comprises a deeply recessed portion of the lower jaw. This portion 144 provides a hinge action at this position along the lower jaw 14 enabling the U-shaped portion 140 to pivot relative to the elongate relatively straight portion 142.

The second hinge 144 will weaken the lower jaw and to compensate for this weakness the U-shaped portion 140 is thickened in cross-section at the end 146 to provide rigidity for a latch portion 148. Latch portion 148 preferably comprises a tooth 150 which, as described hereinafter co-operates with an interlocking tooth 126 on the upper jaw to lock the clip in a closed position.

The upper jaw 12 is preferably substantially flat on its inner surface 122 and convex on its outer surface 124 thus providing a thickening of the upper jaw in its central portion to give added strength and also a better profile to the upper jaw when the clip is closed.

At its end the upper jaw is provided on its upper surface with a tooth 126 and an indent 128 which co-operate with tooth 150 on the bottom jaw 14 to lock the clip in a latched position. The front edge 130 is profiled as shown to provide a slanted surface and the upper part of the silicone lining 18 is tapered at 182 to cover this surface and (see FIG. 3) to mate with the lower lining when the clip is closed.

The clip is biased open by the combination of the hinge 16 and the silicone lining 18, 20 to provide an opening 100 for capture of the Fallopian tube or vas deferens.

With reference now to FIG. 2, the clip is closed by squeezing together the upper and lower jaws.

As the upper jaw contacts the lower jaw the front edge 130 is forced against the front edge 152 of the tooth 150 and on further closure of the clip the U-shaped portion 140 pivots about the second hinge 144 which allows the tooth 126 to slide underneath the tooth 150.

When this occurs the U-shaped portion 140 then springs back into the position shown in FIG. 3. In this position the clip is effectively locked by the engagement between teeth 150 and 126, tooth 150 being received in indent 128.

During the closure action the opening force exerted by the upper jaw 12 on the lower jaw 14 causes the U-shaped portion 140 to rotate and when the tooth 126 of the upper jaw is depressed to underneath the tooth 150 of the lower jaw 14, the U-shaped member rotates back into its previous position. In doing so the hinge latch arrangement is forced into a tighter engagement.

When used for sexual sterilisation, the clip is not normally required to be re-openable. The interlocking teeth 126, 150 prevent any accidental re-opening of the clip by pressure in the direction of arrow 102 and the engagement of upper jaw 12 under lower jaw 14, 140 prevents any accidental re-opening in the direction of arrow 104.

Thus once fitted into position the clip is effectively locked in the closed position and cannot be accidentally dislodged.

The clip can however be used for other purposes such as isolation of the bile duct or blood or other vessels.

The clip, is in normal circumstances to be considered a disposable item. To this end the construction, being from a single piece of plastics material with a single piece lining is extremely economical. Both the jaws 12, 14 and the lining (or linings) 18, 20 are preferably made by a moulding process and the assembly is extremely easy. Preferably a suitable adhesive is used to fix the lining 18, 20 to the jaws 12, 14.

In an alternative embodiment the lining may be present on only one jaw 12 or 14. Preferably the lining will be only on the lower jaw 14 and may require to be of a different shape to compensate for the absence of the lining 18 on the upper jaw. With reference to FIG. 1 a possible alternative shape is indicated by dotted line 20'.

With the lining (20') only on the lower jaw, the clip has a wider opening 100 which may be advantageous for some uses.

The use of a lining on one jaw only additionally simplifies the construction and hence the manufacture of the clip and therefore make the clip cheaper and thus more available as a disposable item.

In a practical clip the dimensions are as follows:
L1 overall height when closed—4 to 6 mm
L2 overall length—12 to 15 mm
L3 length to second hinge—4 mm
L4 thickness of U-shaped position of lower jaw—2 to 3 mm
L5 thickness of upper jaw—3 mm
L6 thickness of lining—1 mm
L7 thickness of lower jaw—2 mm
L8 depth of second hinge—1 to 1.2 mm The dimensions of the lower jaw 14, hinge 144 and u-shaped portion of the lower jaw 140 emphasise the extent to which the U-shaped portion has to pivot in order to engage with the latch member 126,128 on the upper jaw. The lower jaw 14 is substantially weakened by the second hinge 144 and thus without the positive latching mechanism created by the latch 126,150, the upper and lower jaws could possibly be forced apart. However, the positive latching ensures that the jaws cannot be forced apart by any single pressure. Thus pressing the U-shaped member in the direction of arrow 106 will not release the clip.

Similarly, pressure on the clip in the direction of arrows 102,104 will not release the clip.

Thus, by virtue of the action of the second hinge member 144, the clip, once secured, will remain fastened unless it is subjected firstly to a squeezing action between the upper and lower jaws 12,14 and also to a forcing action of the U-shaped latch portion of the lower jaw in the direction of arrow 106. This combination of actions is not possible to create by an accidental pressure mechanism within a human being. Thus, once affixed, the clip, although made from a one piece plastic moulding, will be permanently fixed to the Fallopian tube or vas deferens.

We claim:

1. A sexual sterilisation clip having a lower jaw member and an upper jaw member hingedly connected at one end to the lower jaw member, and comprising an internal silicone rubber lining, the upper and lower jaw members being provided at an opposite end thereof in relation to the hinge, with co-operating latch means comprising interlocking members in the upper and lower jaws to secure the clip in a closed position, the lower jaw being provided with a second hinge proximate to the co-operating latch means which enables the latch end of the lower jaw to pivot at the position of the second hinge.

2. A sexual sterilisation clip as claimed in claim 1 in which the lower jaw comprises an elongate relatively straight portion comprising the main portion of the lower jaw conjoined with a U-shaped portion forming the latch means on the lower jaw, the main and the U-shaped portion being formed by the second hinge.

3. A sexual sterilisation clip as claimed in claim 2 in which the latch means is arranged to lock the clip in a closed position, the clip being re-openable by squeezing the upper and lower jaws together and by pushing the latch formed by the lower jaw off the lower jaw.

4. A sexual sterilisation clip as claimed in claim 1 in which the interlocking members comprise interlocking teeth.

5. A sexual sterilisation clip as claimed in claim 4 in which the upper and lower jaws are both lined internally with the silicone rubber.

6. A sexual sterilisation clip as claimed in claim 4 in which only the upper or lower jaw is lined internally with the silicone rubber.

7. A sexual sterilisation clip as claimed in claim 6 in which only the lower jaw is lined internally with silicone rubber.

8. A sexual sterilisation clip as claimed in claim 2 in which the U-shaped member comprises a substantially thicker cross section to provide a strong latch.

9. A sexual sterilisation clip comprising:

a lower jaw member;

an upper jaw member hingedly connected at one end to the lower jaw member; and an internal silicone rubber lining, wherein said upper and lower jaw members are provided at an opposite end thereof in relation to the hinge with co-operating latch means comprising interlocking members in the upper and lower jaw members to secure the clip in a closed position, the lower jaw member only being provided with a second hinge proximate to the co-operating latch means which enables the latch end of the lower jaw member to pivot at the position of the second hinge, said second hinge being formed by providing a deep recession on the inside of the lower jaw member thereby providing a substantially weaker portion of said lower jaw member which acts as the second hinge.

10. A sexual sterilisation clip comprising:

a lower jaw member;

an upper jaw member hingedly connected at one end to the lower jaw member; and an internal silicone rubber lining, wherein said upper and lower jaw members are provided at an opposite end thereof in relation to the hinge, with co-operating latch means comprising interlocking members in the upper and lower jaw members to secure the clip in a closed position, said interlocking members comprising interlocking teeth which act when interlocked to secure the clip in a closed position whereby to open the clip pressure must be exerted on the clip in a first direction on the upper jaw member and in a second, different direction on the lower jaw member, the lower jaw member only being provided with a second hinge proximate to the co-operating latch means which enables the latch end of the lower jaw member to pivot at the position of the second hinge, the second hinge comprising a deeply recessed portion of said lower jaw member.

* * * * *